(12) United States Patent
Gyorkos et al.

(10) Patent No.: US 6,548,638 B2
(45) Date of Patent: Apr. 15, 2003

(54) PEPTOID AND NONPEPTOID CONTAINING α-KETO OXADIAZOLES AS SERINE PROTEASE INHIBITORS

(75) Inventors: Albert Gyorkos, Westminster, CO (US); Lyle Spruce, Chula Vista, CA (US); Kazuyuki Ohmoto, Osaka (JP); Kazuhito Kawabata, Osaka (JP)

(73) Assignee: Cortech, Inc., Bedminster, NJ (US)

( * ) Notice: Subject to any disclaimer, the term of this patent is extended or adjusted under 35 U.S.C. 154(b) by 90 days.

(21) Appl. No.: 09/842,543

(22) Filed: Apr. 26, 2001

(65) Prior Publication Data

US 2002/0010315 A1 Jan. 24, 2002

Related U.S. Application Data

(63) Continuation of application No. 09/325,512, filed on Jun. 3, 1999, now Pat. No. 6,255,453, which is a continuation-in-part of application No. 09/090,046, filed on Jun. 3, 1998, now Pat. No. 6,001,813, and a continuation-in-part of application No. 09/090,274, filed on Jun. 3, 1998, now Pat. No. 6,001,814.

(51) Int. Cl.[7] .................. A61K 38/05; A61K 38/06; C07K 5/06; C07K 5/08

(52) U.S. Cl. .................. 530/331; 514/18; 514/19; 544/319

(58) Field of Search .................. 514/18, 19; 530/331; 544/319

(56) References Cited

U.S. PATENT DOCUMENTS

| | | | |
|---|---|---|---|
| 4,338,453 A | 7/1982 | Gall | 548/263 |
| 5,055,450 A | 10/1991 | Edwards et al. | 514/19 |
| 5,164,371 A | 11/1992 | Edwards et al. | 514/18 |

(List continued on next page.)

FOREIGN PATENT DOCUMENTS

| | | |
|---|---|---|
| DE | 2 224 338 | 11/1972 |
| EP | 0 291 234 A2 | 11/1988 |
| EP | 0 480 044 A1 | 4/1992 |
| EP | 0 528 633 A1 | 2/1993 |
| EP | 0 529 568 A1 | 3/1993 |
| FR | 2 694 295 | 2/1994 |
| GB | 1 397 073 | 6/1975 |
| WO | WO 93/21212 | 10/1993 |
| WO | WO 95/33762 | 12/1995 |
| WO | WO 96/16080 | 5/1996 |

OTHER PUBLICATIONS

Edwards, et al., Peptidyl a–Ketoheterocyclic Inhibtors of Human Neutrophil Elastase., J. Med. Chem., 1995, 38, p. 3972–3982.

Edwards, et al., Nonpeptidic Inhibitors of Human Neutrophil Elastase., J. Med. Chem., 1996, 39, p. 1112–1124.

Edwards, et al., Peptidyl a–Ketoherocyclic Inhibtors of Human Neutrophil Elastase., J. Med. Chem., 1995, 38, p. 76–85.

Veale, et al., Non–peptidic Inhibtors of Human Leukocyte Elastase., J. Med. Chem., 1995, 38, p. 86–97.

Veale, et al., Nonpeptidic Inhibtors of Human Leukocyte Elastase., J. Med. Chem., 1995, 38, p. 98–108.

(List continued on next page.)

Primary Examiner—Jeffrey E. Russel
(74) Attorney, Agent, or Firm—Bromberg & Sunstein LLP

(57) ABSTRACT

The present invention relates to certain substituted oxadiazole peptoids and nonpeptoids useful as inhibitors of serine proteases, especially human neutophil elastase (HNE). Compounds of the present invention are useful for the treatment or amelioration of symptoms of adult respiratory distress syndrome, septic shock, and multiple organ failure. Processes mediated by HNE are also implicated in conditions such as arthritis, periodontal disease, glomerulonephritis, and cystic fibrosis.

1 Claim, 3 Drawing Sheets

U.S. PATENT DOCUMENTS

| | | | |
|---|---|---|---|
| 5,550,139 A | 8/1996 | Groutes | 514/362 |
| 5,618,792 A | 4/1997 | Gyorkos et al. | 514/18 |
| 5,801,148 A | 9/1998 | Gyorkos et al. | 514/18 |
| 5,807,829 A | 9/1998 | Gyorkos et al. | 514/18 |
| 5,861,380 A | 1/1999 | Gyorkos et al. | 514/19 |
| 5,869,455 A | 2/1999 | Gyorkos et al. | 514/18 |
| 5,874,585 A | 2/1999 | Gyorkos et al. | 548/128 |
| 6,015,791 A | 1/2000 | Gyorkos et al. | 514/18 |
| 6,037,325 A | 3/2000 | Gyorkos et al. | 514/18 |
| 6,150,334 A | 11/2000 | Gyorkos et al. | 514/18 |
| 6,159,938 A | 12/2000 | Gyorkos et al. | 514/17 |

OTHER PUBLICATIONS

Goddard, Antiinflammatory 1–Phenylpyrazole–4– Heteroarylalkanoic Acids., J. Med., Chem., 1991, 28, p. 1607–1612.

LaMattina, et al., Utility of p–Nitrophenyl 3–Bromo–2,2–diethoxypropionate (NPBDP) in Heterocyclic Synthesis., J. Org. Chem., 1984, 49, p. 4800–4805.

Unangst, et al., Novel 1,2,4–Oxadiazoles and 1,2,4–Thiadiazoles as Dual 5–Lipoxygenase and Cyclooxygenase Inhibitors., J. Med. Chem., 1992, 35, p. 3691–3698.

Kitatani, et al., A Novel Oxazole Synthesis Utilizing Tingsten (VI) Catalyzed Decomposition of a–Diazo Carbonyl Compounds in Nitriles., Tetrahedron Letters, 1974, 16, p. 1531–1532.

Wiley, The Chemistry of the Oxazoles., 1945, 37, p. 401–443.

Davidson, et al., The Action of Ammonia on Benzoin., 1937, 2, p. 328–334.

Wiegand, et al., Polyphosphoric Acid Cyclization of Acetamidoketones to 2,5–Dimethyl–1,3–oxazoles., Synthesis, 1970, 12, p. 648–649.

Wasserman, et al., The Oxazole–Triamide Rearrangement., Tetrahedron Letters, 1982, 23(37), p. 3831–3834.

Cornforth, A New Synthesis of Oxazoles and Iminazoles including its Application to the Preparation of Oxazole., J. Chem. Soc., 1947, 96, p. 96–102.

Cornforth, Synthesis of Oxazoles from Ethyl Acetoacetate. J. Chem. Soc., 1953, 93, p. 93–98.

Bernstein, Nonpeptidic Inhibitors of Human Leukocyte Elastase., J. Med. chem., 1994, 37, p. 3313–3326.

Brown, Design of Orally Active, Non–Peptide Inhibitors of Human Leukocyte Elastase., Amer. Chem. Soc., 1994, 37(9), p. 1259–1261.

Warner, et al., J. Med. Chem., Non–Peptidic Inhibitors of Human Leukocyte Elastase., 1994, 37, p. 3090–3099.

Budavari, The Merck Index., Cefazedone, 1989, p. 294.

Damewood, Nonpeptidic Inhibitors of Human Leukocyte Elastase., 1994, 37, p. 3303–3312.

U.S. patent application Ser. No. 09/927,832, Gyorkos et al., filed Aug. 10, 2001.

U.S. patent application Ser. No. 09/928,117, Gyorkos et al., filed Aug. 10, 2001.

U.S. patent application Ser. No. 10/125,222, Gyorkos et al., filed Apr. 18, 2002.

PEPTOID AND NONPEPTOID CONTAINING α-KETO OXADIAZOLES AS SERINE PROTEASE INHIBITORS

This application is a continuation application of U.S. Ser. No. 09/325,512, filed Jun. 3, 1999, now U.S. Pat. No. 6,255,453, which is a continuation in part of U.S. Ser. No. 09/090,046, filed Jun. 3, 1998, now U.S. Pat. No. 6,001,813; and U.S. Ser. No. 09/090,274 filed Jun. 3, 1998, now U.S. Pat. No. 6,001,814 all three of which are incorporated herein by reference.

BACKGROUND OF THE INVENTION

The serine proteases are a class of enzymes, which includes elastase, chymotrypsin, cathepsin G, trypsin and thrombin. These proteases have in common a catalytic triad consisting of Serine-195, Histidine-57 and Aspartic acid-102(chymotrypsin numbering system). Human neutrophil elastase (HNE) is a proteolytic enzyme secreted by polymorphonuclear leukocytes (PMNs) in response to a variety of inflammatory stimuli. This release of HNE and its extracellular proteolytic activity are highly regulated and are normal, beneficial functions of PMNs. The degradative capacity of HNE, under normal circumstances, is modulated by relatively high plasma concentrations of $\alpha_1$-proteinase inhibitor ($\alpha$-PI). However, stimulated PMNs produce a burst of active oxygen metabolites, some of which (hypochlorous acid for example) are capable of oxidizing a critical methionine residue in $\alpha$-PI. Oxidized $\alpha$-PI has been shown to have limited potency as an HNE inhibitor and it has been proposed that alteration of this protease/antiprotease balance permits HNE to perform its degradative functions in localized and controlled environments.

Despite this balance of protease/antiprotease activity, there are several human disease states in which a breakdown of this control mechanism is implicated in the pathogenesis of the condition. Improper modulation of HNE activity has been suggested as a contributing factor in adult respiratory distress syndrome, septic shock and multiple organ failure. A series of studies also have indicated the involvement of PMNs and neutrophil elastase in myocardial ischemia-reperfusion injury. Humans with below-normal levels of $\alpha_1$-PI have an increased probability of developing emphysema. HNE-mediated processes are implicated in other conditions such as arthritis, periodontal disease, glomerulonephritis, dermatitis, psoriasis, cystic fibrosis, chronic bronchitis, atherosclerosis, Alzheimer's disease, organ transplantation, corneal ulcers, and invasion behavior of malignant tumors.

There is a need for effective inhibitors of HNE as therapeutic and as prophylactic agents for the treatment and/or prevention of elastase-mediated problems.

SUMMARY OF THE INVENTION

In one embodiment, the present invention provides compounds of formula I wherein X and Y are independently O or N;

$R_1$ is alkyl, $\alpha$, $\alpha$-dialkylalkylaryl or $\alpha$, $\alpha$-dialkylalkyl fused aryl-cycloalkyl wherein the cycloalkyl group is optionally substituted with two or more O atoms;

$R_2$ and $R_3$ are independently H or alkyl; or together form a ring consisting of 3–5 carbons in which one or more carbon atoms of the ring can optionally be replaced with heteroatoms selected from O, S or N wherein N is optionally substituted with H or alkyl, preferably one of $R_2$ and $R_3$ is H and the other is iso-propyl; and $R_4$ is alkyloxycarbonyl.

Preferably, compounds of the present invention comprise a 1,3,4 oxadiazole ring (i.e., X is N; Y is O).

In one preferred embodiment of the invention, $R_1$ is alkyl, such as tert-butyl. In another embodiment, $R_1$ is $\alpha,\alpha$-dialkylalkylaryl, such as an $\alpha$, $\alpha$-dimethylbenzyl group. In still another preferred embodiment, $R_1$ is $\alpha$, $\alpha$-dialkylalkyl fused aryl-cycloalkyl wherein the cycloalkyl group is substituted with two O atoms, such as an $\alpha,\alpha$-dimethyl-(3,4-methylenedioxy)benzyl group. In yet another preferred embodiment, $R_2$ and $R_3$ are independent alkyl, such as isopropyl, or H. Preferably, $R_2$ is isopropyl and $R_3$ is H.

In another embodiment, the present invention provides compounds of formula II:

wherein X and Y are independently O or N;

$R_1$, $R_2$, and $R_3$ are as above;

$R'_2$ and $R'_3$ are independently H or alkyl; or together form a ring consisting of 3–5 carbon atoms in which one or more carbon atoms of the ring can optionally be replaced by heteroatoms selected from O, S or N, wherein N is optionally substituted with H or alkyl;

A is a direct bond, —NH— or —OC(O)—NH—;

$R_4$ is H or halo; and $R_5$ is H, alkyl or arylalkyl; or a pharmaceutically acceptable salt thereof.

Preferably, compounds of this embodiment of the present invention comprise a 1,3,4 oxadiazole ring (i.e., X is N; Y is O).

In one preferred embodiment of the invention, $R_1$ is alkyl, such as tert-butyl. In another embodiment, $R_1$ is $\alpha,\alpha$-dialkylalkyl fused aryl-cycloalkyl wherein the cycloalkyl group is substituted with two O atoms, such as an $\alpha,\alpha$-dimethyl-(3,4-methylenedioxy)benzyl group. In yet another embodiment, $R_1$ is $\alpha,\alpha$-dialkylalkylaryl, such as an $\alpha,\alpha$-dimethylbenzyl group. In still another preferred embodiment, $R_2$ and $R_3$ are independently alkyl, such as isopropyl, or H. In a more preferred embodiment, $R_2$ is isopropyl, $R_3$ is H, and $R_2'$ and $R_3'$ are both H. Where $R_4$ is halo, $R_4$ may be Cl, F, I or Br, although preferably it is F.

As used herein, the term "optionally substituted" means, when substituted, mono to fully substituted.

As used herein, the term "independently" means that the substituents may be the same or different.

As used herein, the term "alkyl" means $C_1$–$C_{15}$, and preferably $C_1$–$C_8$. It will be understood that the alkyl group may be linear or branched.

As used herein, the term "α,α-dialkylalkylaryl" means that the alkyl groups are substituted at the α-positions to the oxadiazole ring or to the aryl group or both. One such example is an α,α-dialkylbenzyl, wherein the α-substituents are preferably methyl, ethyl or propyl. A specific example is α,α-dimethylbenzyl. The term "α,α-dialkylalkyl fused aryl-cycloalkyl" is defined to mean that the alkyl groups are substituted at the α-positions to the oxadiazole ring or to the aryl group, and a cycloalkyl is fused to the aryl ring. One such example of an "α,α-dialkylalkyl fused aryl-cycloalkyl" is an α,α-dialkyl-3,4-methylenedioxybenzyl group, wherein the α-substituents are preferably methyl, ethyl or propyl; preferably they are methyl. A specific example includes the α,α-dimethyl-3,4-methylenedioxybenzyl group.

As used herein, the term alkyloxycarbonyl means alkyl-O—C(O)— wherein the meaning of alkyl is defined above. One such example of an alkyloxycarbonyl is methyloxycarbonyl and is defined by the formula $CH_3$—O—C(O)—.

DETAILED DESCRIPTION

Figure 1:
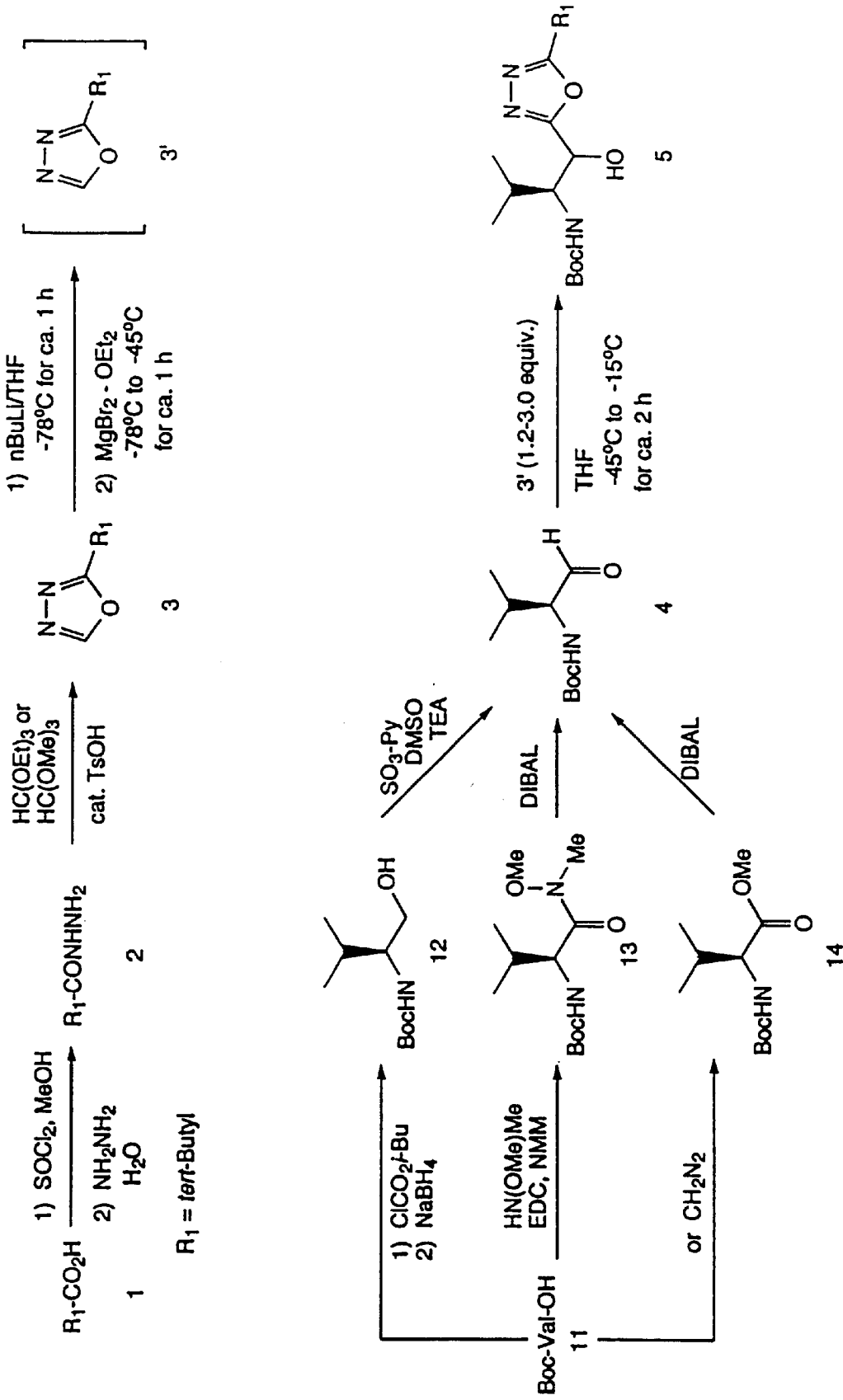
FIG. 1 is a schematic representation of the synthetic scheme for the Boc protected amino alcohol intermediates used in the invention.

The compounds of the present invention have been found to be potent inhibitors of the serine protease human neutrophil elastase (HNE). They are reversible inhibitors that presumably form a transition state intermediate with the active site serine residue. The compounds are characterized by their low molecular weights, high selectivity with respect to HNE and stability regarding physiological conditions. Therefore, the compounds can be implemented to prevent, alleviate and/or otherwise treat diseases, which are mediated by the degradative effects associated with the presence of HNE. Their usage is of particular importance as they relate to various human treatment in vivo but may also be used as a diagnostic tool in vitro.

The present invention provides, but is not limited to, specific embodiments set forth in the Examples as well as those set forth below.

The nomenclature for the embodiments is as follows (although embodiments disclosed indicate the stereochemistry of the 2-methylpropyl group as having the (S)-configuration, it will be understood that both the enantiomerically pure (R) and racemic (R,S) configurations are within the scope of the invention):

Example 1 Methyloxycarbonyl-L-valyl-N-[1-(2-[5-(tert-butyl)oxadiazolyl]carbonyl)-2-(S)-methylpropyl]-L-prolinamide.

Example 2 Methyloxycarbonyl-L-valyl-N-[1-(2-[5-(α,α-dimethylbenzyl)oxadiazolyl]carbonyl)-2-(S)-methylpropyl]-L-prolinamide.

Example 3 Methyloxycarbonyl-L-valyl-N-[1-(2-[5-(α,α-dimethyl-3,4-methylenedioxybenzyl)-1,3,4-oxadiazolyl]carbonyl)-2-(S)-methylpropyl]-L-prolinamide.

Example 4 2-[6-Oxo-2-(4-fluorophenyl)-1,6-dihydro-1-pyrimidinyl]-N-[1-(2-[5-tert-butyl 1,3,4-oxadiazolyl]carbonyl)-2-(S)-methylpropyl]acetamide.

Example 5 2-[5-Benzyloxycarbonylamino-6-oxo-2-(4-fluorophenyl) 1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide.

Example 6 2-[5-Amino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(R, S)-methylpropyl]acetamide.

Example 7 2-[5-Benzyloxycarbonylamino-6-oxo-2-phenyl-1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide.

Example 8 2-[5-Amino-6-oxo-2-phenyl-1,6-dihydro-1-pyrimidinyl]-N-[1-(2-[5-(α,α-dimethyl-3,4methylenedioxybenzyl)-1,3,4-oxadiazolyl]carbonyl)-2-(R, S)-methylpropyl]acetamide.

Example 9 2-[6-Oxo-2-phenyl-1,6-dihydro-1-pyrimidinyl]-N-[1-(2-[5-(α,α-dimethyl-3,4-methylenedioxybenzyl)-1,3,4-oxadiazolyl]carbonyl)-2-(R, S)-methylpropyl]acetamide.

Example 10 2-[6-Oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(R, S)-methylpropyl]acetamide.

Example 11 2-[6-Oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(R,S)-methylpropyl]acetamide.

Example 12 2-[6-Oxo-2-phenyl-1,6-dihydro-1-pyrimidinyl]-N-[1-(2-[5-(α,α-dimethylbenzyl)-1,3,4-oxadiazolyl]carbonyl)-2-(R,S)-methylpropyl]acetamide.

Example 13 2-[5-Methyloxycarbonylamino-6-oxo-2-phenyl-1,6-dihydro-1-pyrimidinyl]-N-[1-(2-[5-(tert-butyl)-1,3,4-oxadiazolyl]carbonyl)-2-(R,S)-methylpropyl]acetamide.

The compounds of the present invention are not limited to use for inhibition of human elastase. Elastase is a member of the class of enzymes known as serine proteases. This enzyme class also includes, for example, chymotrypsin, cathepsin G, trypsin and thrombin. These proteases have in common a catalytic triad consisting of Serine-195, Histidine-57 and Aspartic acid-102 (chymotrypsin numbering system). The precise hydrogen bond network that exists between these amino acid residues allows the Serine-195 hydroxyl to form a tetrahedral intermediate with the carbonyl of an amide substrate. The decomposition of this intermediate results in the release of a free amine and the acylated enzyme. In a subsequent step, this newly formed ester is hydrolyzed to give the native enzyme and the carboxylic acid. It is this carboxyl component that helps characterize the specificity for the enzyme. In the example in which the carboxyl component is a peptide, the alpha-substituent of the amino acid is predominately responsible for the specificity toward the enzyme. Utilizing the accepted nomenclature by Schechter and Berger (*Biochem. Biophy. Res. Commun.*, 27:157 (1967) and *Biochem. Biophys. Res. Commun.*, 32:898 (1968)), the amino acid residues in the substrate that undergo the cleavage are defined as $P_1 \ldots P_n$ toward the N-terminus and $P_1' \ldots P_n'$ toward the C-terminus. Therefore, the scissile bond is between the $P_1$ and the $P_1'$ residue of the peptide subunits. A similar nomenclature is utilized for the amino acid residues of the enzyme that make up the binding pockets accommodating the subunits of the substrate, where the binding pocket for the enzyme is designated by $S_1 \ldots S_n$ instead of $P_1 \ldots P_n$ as for the substrate.

The characteristics for the $P_1$ residue defining serine proteinase specificity is well established. The proteinases may be segregated into three subclasses: elastases, chymases and tryptases based on these differences in the $P_1$ residues. The elastases prefer small aliphatic moieties such as valine whereas the chymases and tryptases prefer large aromatic hydrophobic and positively charged residues respectively.

One additional proteinase that does not fall into one of these categories is propyl endopeptidase. The $P_1$ residue defining the specificity is a proline. This enzyme has been implicated in the progression of memory loss in Alzheimer's patients. Inhibitors consisting of α-keto heterocycles have recently been shown to inhibit propyl endopeptidase (Tsutsumi et al., *J. Med. Chem.*, 37, 3492–3502 (1994)). By way of extension, α-keto heterocycles as defined herein allow for an increased binding in P' region of the enzyme.

TABLE 1

$P_1$ Characteristics for Proteinase Specificity

| Proteinase Class | Representative Enzyme | $P_1$ Characteristic |
|---|---|---|
| Elastases | Human Neutrophil Elastase | small aliphatic residues |
| Chymases | alpha-Chymotrypsin, Cathepsin G | aromatic or large hydrophobic residues |
| Tryptases | Thrombin, Trypsin, Urokinase, Plasma Kallikrein, Plasminogen Activator, Plasmin | positively charged residues |
| Other | Prolyl Endopeptidase | proline |

Since the $P_1$ residue predominately defines the specificity of the substrate, the present invention relates to $P_1$–$P_n'$ modifications, specifically, certain alpha-substituted ketoheterocycles composed of 1,2,4 oxadiazoles and 1,3,4-oxadiazoles. By altering the alpha-substituent to the ketone and, to some extent, the substituent on the heterocycle, the specificity of these compounds can be directed toward the desired proteinase (e.g., small aliphatic groups for elastase).

The efficacy of the compounds for the treatment of various diseases can be determined by scientific methods, which are known in the art. The following are noted as examples for HNE mediated conditions:

for acute respiratory distress syndrome, the method according to human neutrophil elastase (HNE) model (*AARD*, 141:227–677 (1990)); the endotoxin induced acute lung injury model in minipigs (*AARD*, 142:782–788 (1990)); or the method according to human polymorphonuclear elastase-induced lung hemorrhage model in hamsters (European Patent Publication No. 0769498) may be used;

in ischemia/reperfusion, the method according to the canine model of reperfusion injury (*J. Clin. Invest.*, 81: 624–629 (1988)) may be used. The compounds of the present invention, salts thereof, and their intermediates can be prepared or manufactured as described herein or by various processes known to be present in the chemical art (see e.g., WO 96/16080).

Figure 2:
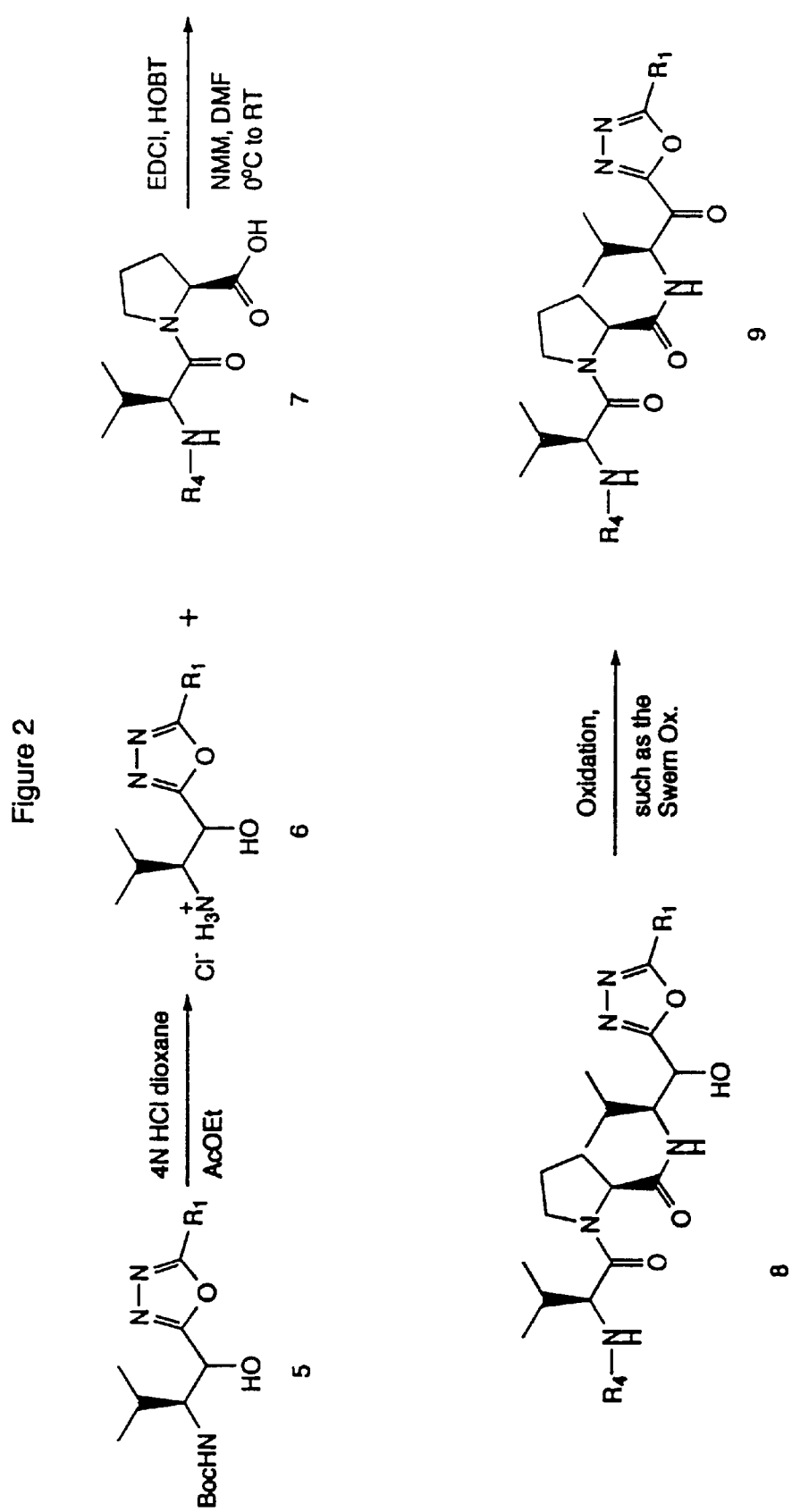
FIG. 2 is a schematic representation of the synthetic scheme for the compounds of one embodiment of the invention.
Figure 3:
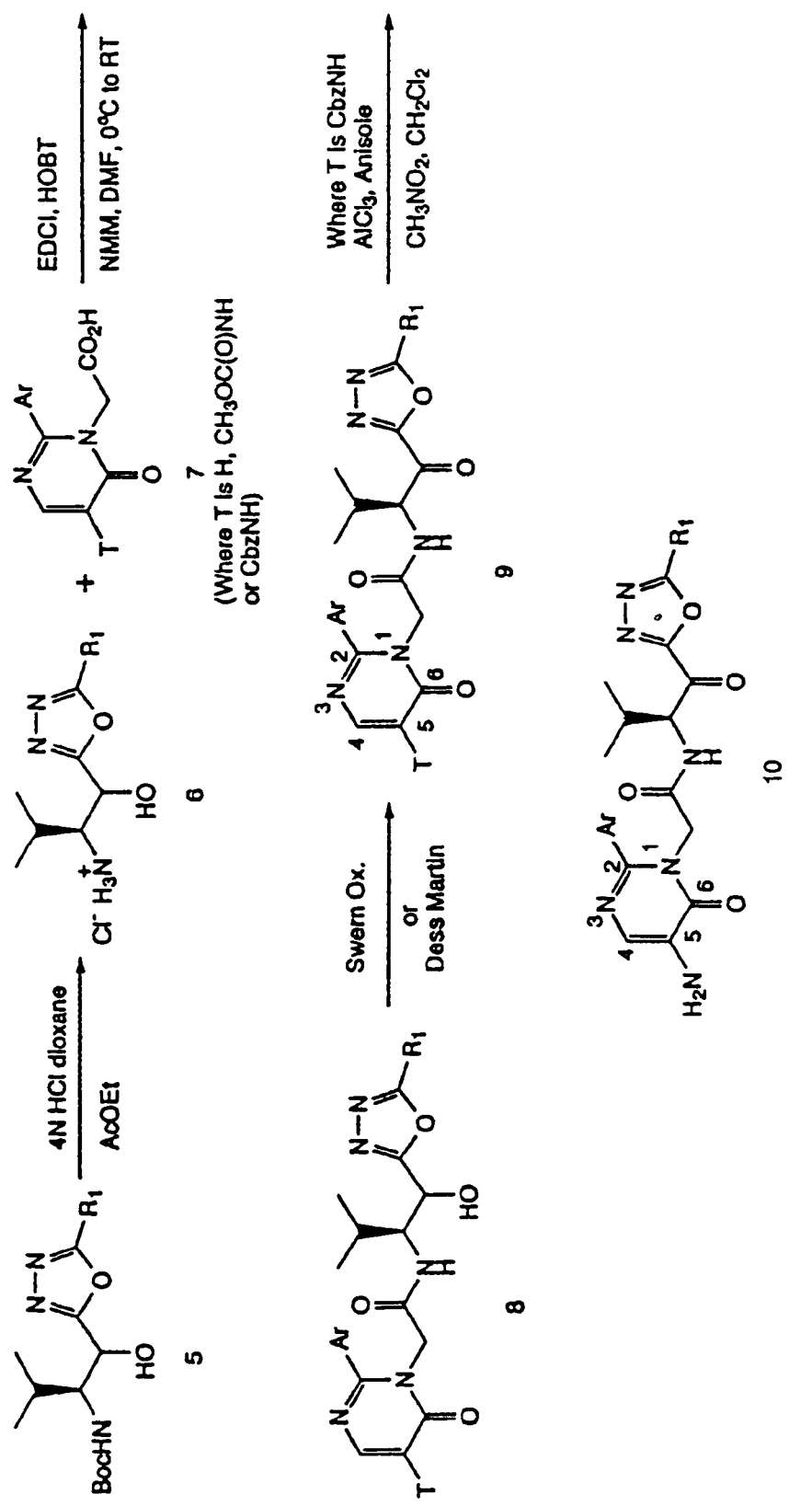
FIG. 3 is a schematic representation of the synthetic scheme for the compounds of another embodiment of the invention.

Alternatively, the compounds of the present invention may be prepared as described in FIGS. 1, 2 and 3. FIG. 1 relates to the synthesis of the Boc protected amino alcohol intermediates used in the invention. FIGS. 2 and 3 show the use of the intermediates for the synthesis compounds of the invention.

The 2-substituted 1,3,4-oxadiazoles (3) may be prepared via formation of methyl esters from the corresponding acids (1) utilizing, for example, thionyl chloride and methanol, followed by treatment with hydrazine in a suitable solvent to yield hydrazonic acids (2). Alternatively, esters can be prepared by methods known to one skilled in the art or those methods described in Comprehensive Organic Transformations (R. Larock, VCH Publishers 1989, 966–972). Reaction of (2) with triethyl orthoformate or trimethyl orthoformate and TsOH gives the requisite 2-substituted 1,3,4-oxadiazoles (3).

Intermediate (3') can be formed utilizing standard conditions (e.g., butyllithium or other known alkyl lithium reagents, at low temperature in a polar aprotic solvent, and further, if desired, reacting with $MgBr.OEt_2$) and subsequently added to aldehyde (4) to give alcohol (5).

The aldehyde (4) may be prepared via any of three methods as described in FIG. 1. One method reduces the intermediate that is formed between Boc-Val-OH and isopropylchloroformate with sodium borohydride to give Boc-Valinol (12). In a subsequent step, the Boc-Valinol is oxidized with $SO_3$-Py in DMSO to give aldehyde (4). Another such method takes the Weinreb amide (13) that is prepared from Boc-Val-OH (11) and reduces it to the aldehyde using diisobutylaluminum hydride (DIBAL). Alternatively, one may generate the ester (14) of the amino acid followed by reduction with DIBAL to afford aldehyde (4).

As shown in FIGS. 2 and 3, deprotection of amine (5) using hydrochloric acid in dioxane gives the amino hydrochloride (6), which is then coupled to the desired acid (7) or (7') by methods available to one skilled in the art to give intermediate (8) or (8'). Oxidation using the Swerm Oxidation, Dess-Martin's Periodinane or other methods as described in Oxidation in Organic Chemistry (M. Hudlicky, ACS Monograph 186 (1990)) yields the desired ketone (9) or (9').

Where a compound is substituted at the 5 position of the pyrimidinone group with a benzyloxycarbonylamino group, a deprotection step can be conducted as described in FIG. 3. This step requires removal of the protecting group from the amine and may be carried out by a number of methods. For example, one may utilize aluminum chloride, anisole and nitromethane in a suitable solvent such as dichloromethane to give the 5-amino compound (10'). Other methods of deprotection available in the art may also be used.

Although the compounds described herein may be administered as pure chemicals, it is preferable to present the active ingredient as a pharmaceutical composition. The invention thus further provides the use of a pharmaceutical composition comprising one or more compounds together with one or more pharmaceutically acceptable carriers thereof and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds may also be formulated for parenteral administration (e.g., by injection, for example, bolus injection or continuous infusion) and may be presented in unit dose form in ampules, pre-filled syringes, small bolus infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. No. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg/day, e.g., from about 1 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form, for example, containing 0.5 to 1000 mg, conveniently 5 to 750 mg, and most conveniently, 10 to 500 mg of active ingredient per unit dosage form.

Ideally, the active ingredient should be administered to achieve peak plasma concentrations of the active compound of from about 0.5 to about 75 $\mu$M, more preferably, about 1 to 50 $\mu$M, and most preferably, about 2 to about 30 $\mu$M. This may be achieved, for example, by the intravenous injection of a 0.05 to 5% solution of the active ingredient, optionally in saline, or orally administered as a bolus containing about 0.5–500 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may be conveniently presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The following examples are given to illustrate the invention and are not intended to be inclusive in any manner.

EXAMPLES

The compounds of the present invention, salts thereof, and their intermediates can be prepared or manufactured as described herein or by various processes known to be present in the chemical art. By way of an example, the final step in the process defined here, is an oxidation of a 2° alcohol to a ketone. As described here, this transformation from an alcohol to ketone was preformed using dimethylsulfoxide and oxalyl chloride followed by base, which is known as the Swern oxidation. However, modifications of the Swern oxidation are known in the art and are acceptable in this present invention. It is known that alternative electrophilic molecules can be substituted for oxalyl chloride such as dicyclohexylcarbodiimide, acetic anhydride, trifluoroacetic anhydride or sulfur trioxide (Mancuso et al., Synthesis 165 (1981)). Alternatively, other oxidative methods can be used such as N-chlorosuccinimide (NCS) followed by base as described by the inventors in U.S. Pat. No. 5,618,792 or periodinane such as the Dess-Martin reagent. Still other methods may also be appropriate as described in Oxidation in Organic Chemistry (M. Hudlicky, ACS Monograph 186 (1990)).

Besides the methods described below, other methods can be used for making substituted oxadiazole nonpeptides. U.S. Pat. No. 5,807,829, incorporated herein by reference, teaches some other methods for making substituted oxadiazole nonpeptides.

The skilled artisan will understand that where a particular enantiomer is mentioned, the mirror-image enantiomer or a mixture of enantiomers can be used.

Symbols have the standard meanings as familiar to one skilled in the art, by way of example the following have been used: ml (milliliters), g (grams), TLC (thin layer chromatography), $R_f$ (the ratio of the distance moved by a compound to the distance that the solvent front moved during the same time on a TLC plate), $^1$H NMR (proton nuclear magnetic resonance), DMSO-d6 (deuterodimethylsulfoxide) and $CDCl_3$ (deuterochloroform).

Example 1

Methyloxycarbonyl-L-valyl-N-[1-(2-[5-(tert-butyl)-oxadiazolyl]carbonyl)-2-(S)-methylpropyl]-L-prolinamide The secondary alcohol, methyloxycarbonyl-L-valyl-N-[1-(2-[5-(tert-butyl)-oxadiazolyl]hydroxymethyl)-2-(S)-methylpropyl]-L-prolinamide, was oxidized using one of the methods known to one skilled in the art, such as, Swern Oxidation. The intermediate methyloxycarbonyl-L-valyl-N-[1-(2-[5-(tert-butyl)-oxadiazolyl]hydroxymethyl)-2-(S)-methylpropyl]-L-prolinamide was prepared as follows:

A. tert-Butylcarbohydrazonic acid

The mixture of methyl trimethylacetate (230 ml) and hydrazine monohydrate (170 ml) was refluxed for 24 hours. The reaction was cooled to room temperature, and concentrated under reduced pressure. The residue was azeotroped with toluene several times, dissolved in a saturated aqueous solution of sodium chloride, and extracted with chloroform (4×). The extract was dried over anhydrous sodium sulfate, and concentrated under reduced pressure to give tert-butylcarbohydrazonic acid (176 g) having the following physical data.

TLC: $R_f$=0.59, chloroform: methanol (10:1).
$^1$H NMR (DMSO-$d_6$): δ8.78 (1H, brs), 4.15 (2H, brs), 1.08 (9H, s).

B. 2-tert-Butyl-1,3,4-oxadiazole

The mixture consisting of tert-butylcarbohydrazonic acid (176 g), trimethyl orthoformate (250 ml) and p-toluenesulfonic acid monohydrate (4.3 g) was heated and methanol removed by distillation at a temperature ranging from 90° C. to 110° C. Trimethyl orthoformate was removed (50° C./43 mm Hg) and the residue was distilled at 120° C./23 mm Hg to give 2-tert-Butyl-1,3,4-oxadiazole (131 g) having the following physical data.

TLC: $R_f$=0.68, chloroform: methanol (10:1).
$^1$H NMR (DMSO-$d_6$): δ9.12(1H, s), 1.36 (9H, s).

C. 1-[2-(5-tert-Butyl)-1,3,4-oxadiazolyl]-2-(S)-(tert-butoxycarbonylamino)-3-methylbutan-1-ol To a solution of 2-tert-Butyl-1,3,4-oxadiazole (62.1 g) in tetrahydrofuran (1650 ml) was added n-butyllithium in hexane (1.6 M, 307.8 ml) dropwise at −78° C. under an atmosphere of argon. The mixture was stirred for 40 min at −78° C., magnesium bromide diethyl etherate (127.2 g) was added, and the resulting mixture was allowed to warm to −45° C. After 1.5 hours, a solution of 2-(S)-[N-(tert-butoxycarbonyl)amino]-3-methylbutanal (90 g) in tetrahydrofuran (60 ml) was added dropwise at −45° C. and allowed to warm to −15° C. The reaction mixture was quenched by addition of a saturated aqueous solution of ammonium chloride, and extracted with ethyl acetate. The extract was washed with water (x3) and a saturated aqueous solution of sodium chloride, dried over anhydrous sodium sulfate and concentrated. The residue was purified by column chromatography on silica gel (Merck 7734) (ethyl acetate:hexane= 1:20 to 1:1) to give 1-[2-(5-tert-butyl-1,3,4-oxadiazolyl]-2-(S)-tert-butoxycarbonylamino)-3-methylbutan-1-ol (78.6 g) having the following physical data.

TLC: $R_f$=0.42, hexane:ethyl acetate (1:1).
$^1$H NMR (CDCl$_3$): δ5.16–4.90 (2H, m), 4.67 (1H, m), 4.23 (1H, m), 3.90 (1H, m), 3.66 (1H, m), 1.98 (1H, m), 1.42, 1.41 and 1.36 (total 18H, each s), 1.13–0.90 (6H, m).

D. 1-[2-(5-tert-Butyl-1,3,4-oxadiazolyl]-2-(S)-amino-3-methylbutan-1-ol Hydrochloride To a solution of 1-[2-(5-tert-butyl-1,3,4-oxadiazolyl]-2-(S)-(tert-butoxycarbonylamino)-3-methylbutan-1-ol (76.3 g) in dioxane (200 ml) was added 4N hydrochloric acid in dioxane solution (1000 ml) at 0° C. The reaction mixture was concentrated under reduced pressure. The residue was solidified with diethyl ether. The solid was azeotroped with benzene several times to give 1-[2-(5-tert-butyl)-1,3,4-oxadiazolyl]-2-(S)-amino-3-methylbutan-1-ol hydrochloride (66.1 g) having the following physical data.

TLC: $R_f$=0.30, chloroform:methanol (10:1);
$^1$H NMR (CDCl$_3$): δ8.50–8.10 (2H, br), 7.10–6.80 (1H, br), 5.55–5.35 (1H, m), 3.95–3.60 (2H, m), 2.10 (1H, m), 1.41 (9H, s), 1.20–1.00 (6H, m).

E. Methyloxycarbonyl-L-valyl-N-[1-(2-[5-(tert-butyl)-oxadiazolyl]hydroxymethyl)-2-(S)-methylpropyl]-L-prolinamide Prepared using methyloxycarbonyl-L-Val-Pro-OH and 1-[2-(5-tert-Butyl)-1,3,4-oxadiazolyl]-2-(S)-amino-3-methylbutan-1-ol hydrochloride and a coupling method know to one skilled in the art.

The product had the following physical data.

TLC: $R_f$=0.58, ethyl acetate.
$^1$H NMR: (200 MHz, CDCl$_3$), δ7.53 (brd, J=6.2 Hz, 1H, NH), δ5.45–5.29 (m 2H, NH, and α CH of $P_1$ Val), δ4.79–4.62 (m, 1H, α CH of Pro), 4.32 (m, 1H, α CH of $P_3$-Val), 3.83–3.51 (m, 2H, NCH$_2$ of Pro), 3.68 (s, 3H, CH$_3$O), 2.55–1.80 (m, 6H, CHs of iso-Pr, and CH$_2$CH$_2$ of Pro), 1.47 (s, 9H, CH$_3$s of t-Bu), 1.16–0.86 (m, 12H, CH$_3$s of iso-Pr).

Example 2

Methyloxycarbonyl-L-valyl-N-[1-(2-[5-(α,α-dimethylbenzyl)-oxadiazolyl]carbonyl)-2-(S)-methylpropyl]-L-prolinamide The compound was prepared by oxidizing methyloxycarbonyl-L-valyl-N-[1-(2-[5-(α,α-dimethylbenzyl)-oxadiazolyl]hydroxymethyl)-2-(S)-methylpropyl]-L-prolinamide using a procedure know to one skilled in the art, such as, Swern Oxidation.

The intermediate, methyloxycarbonyl-L-valyl-N-[1-(2-[5-(α,α-dimethylbenzyl)-oxadiazolyl]hydroxymethyl)-2-(S)-methylpropyl]-L-prolinamide, was prepared using methyloxycarbonyl-L-Val-Pro-OH and 1-[2-(α,α-dimethylbenzyl)-1,3,4-oxadiazolyl]-2-(S)-amino-3-methylbutan-1-ol hydrochloride and a coupling method know to one skilled in the art. The intermediate 1-[2-(α,α-dimethylbenzyl)-1,3,4-oxadiazolyl]-2-(S)-amino-3-methylbutan-1-ol hydrochloride was prepared using a similar procedure as described in Example 1 except methyl phenylisobutyrate was used instead of methyl trimethylacetate.

The product had the following physical data.

TLC: $R_f$=0.64, ethyl acetate.
$^1$H NMR (200 MHz, CDCl$_3$), 7.84 and 7.49 (each brd., J=7.6 Hz, totally 1H, NH), 7.40–7.20 (m 5H aromatic Hs), 5.46–5.29 (m, 2H, NH, and α CH of $P_1$ Val), 4.77–4.60 (m, 1H, α CH of Pro), 4.40–4.25 (m, 1H, α CH of $P_3$ Val), 3.84–3.55 (m, 2H, NCH$_2$ of Pro), 3.68 (s, 3H, CH$_3$O), 2.55–1.76 (m, 6H, CHs of iso-Pr and CH$_2$CH$_2$ of Pro), 1.88 (s, 6H, hetC(CH$_3$)$_2$Ph), 1.12–0.82 (m, 12H, CH$_3$s of iso-Pr).

Example 3

Methyloxycarbonyl-L-valyl-N-[1-(2-[5-(α,α-dimethyl-3,4-methylene-dioxybenzyl)-1,3,4-oxadiazolyl]carbonyl)-2-(S)-methylpropyl]-L-prolinamide The compound was prepared by oxidizing methyloxycarbonyl-L-valyl-N-[1-(2-[5-(α,α-dimethyl-3,4-methylenedioxybenzyl)-oxadiazolyl]hydroxymethyl)-2-(S)-methylpropyl]-L-prolinamide using a procedure know to one skilled in the art, such as, Swern Oxidation.

The intermediate, methyloxycarbonyl-L-valyl-N-[1-(2-[5-(α,α-dimethyl-3,4-methylenedioxybenzyl)-oxadiazolyl]

hydroxymethyl)-2-(S)-methylpropyl]-L-prolinamide, was prepared using methyloxycarbonyl-L-Val-Pro-OH and 1-[2-(α,α-dimethyl-3,4-methylenedioxybenzyl)-1,3,4-oxadiazolyl]-2-(S)-amino-3-methylbutan-1-ol hydrochloride and a coupling method know to one skilled in the art. The intermediate 1-[2-(α,α-dimethyl-3,4-methylenedioxybenzyl)-1,3,4-oxadiazolyl]-2-(S)-amino-3-methylbutan-1-ol hydrochloride was prepared using a similar procedure as described in Example 1 except methyl 3,4-methylenedioxyphenylisobutyrate was used instead of methyl trimethylacetate.

The product had the following physical data.

TLC: $R_f$=0.63, ethyl acetate.

$^1$H NMR (200 MHz, CDCl$_3$): 7.49 (d, J=6.4 Hz, 1H, NH), 6.85–6.73 (m, 3H, aromatic Hs), 5.95 (s, 2H, OCH$_2$O), 5.46–5.28 (m, 1H α CH of Pro), 4.30 (m, 1H, α CH of P$_3$-Val), 3.84–3.54 (m, 2H, NCH$_2$ of Pro), 3.68 (s, 3H, CH$_3$O), 2.55–1.78 (m, 6H, CHs of iso-Pr, and CH$_2$CH$_2$ of Pro), 1.83 (s, 6H, HetC(CH$_3$)2Ph), 1.11–0.85 (m, 12H, CH$_3$s of iso-Pr).

Example 4

2-[6-Oxo-2-(4-fluorophenyl)-1,6-dihydro-1-pyrimidinyl]-N-[1-(2-[5-tert-butyl-1,3,4-oxadiazolyl] carbonyl)-2-(S)-methylpropyllacetamide To a solution of oxalyl chloride (5.80 ml) in dichloromethane (160 ml) was slowly added dropwise a solution of dimethylsulfoxide (9.44 ml) in dichloromethane (16 ml) at −78° C. under an atmosphere of argon. The mixture was stirred for 30 min at 78° C. To the mixture was added dropwise a solution of 2-[6-Oxo-2-(4-fluorophenyl)-1,6-dihydro-1-pyrimidinyl]-N-[1-(2-[5-tert-butyl-1,3,4-oxadiazolyl]hydroxymethyl)-2-(S)-methylpropyl]acetamide (15.2 g) in dichloromethane (160 ml) at −78° C. The mixture was stirred for 2 hours at −78° C. To the resulting solution was added triethylamine (97.2 ml) dropwise at −78° C. The reaction mixture was warmed up to room temperature, and stirred for 34 hours at the same temperature. The reaction mixture was acidified by addition of 2N aqueous solution of hydrochloric acid, and extracted with dichloromethane. The extract was washed with 2N aqueous solution of hydrochloric acid, water and a saturated aqueous solution of sodium chloride, dried over anhydrous sodium sulfate, and concentrated. The residue was purified by column chromatography on silica gel using a gradient elution of 66 to 100% ethyl acetate/hexane to give 2-[6-oxo-2-(4-fluorophenyl)-1,6-dihydro-1-pyrimidinyl]-N-[1-(2-[5-tert-butyl-1,3,4-oxadiazolyl]carbonyl)-2-(S)-methylpropyl]acetamide (10.92 g) having the following physical data.

TLC: $R_f$=0.63, chloroform:methanol (10:1).

$^1$H NMR (CDCl$_3$): δ 8.00(1H, d, J=6.5 Hz), 7.64 (2H, dd, J=8.6, 5.4 Hz), 7.17 (2H, t, J=8.6 Hz), 6.95 (1H, brd, J=8.4 Hz), 6.50 (1H, d, J=6.5 Hz), 5.43 (IH, dd, J=8.4, 4.8 Hz), 4.63 and 4.58 (each 1H, each d, J=15.4 Hz), 2.53 (IH, m), 1.48 (9H, s), 1.09 (3H, d, J=6.8 Hz), 0.90 (3H, d, J=6.8 Hz). The intermediate 2-[6-Oxo-2-(4-fluorophenyl)-1,6-dihydro-1-pyrimidinyl]-N-[1-(2-[5-tert-butyl-1,3,4-oxadiazolyl] hydroxymethyl)-2-(S)-methylpropyl]acetamide was prepared as follows:

A. tert-Butylcarbohydrazonic acid t-Butylcarbohydrazonic acid was prepared as described above.

TLC: $R_f$=0.59, chloroform:methanol (10:1).

$^1$H NMR (DMSO-d$_6$): δ 8.78 (1H, brs), 4.15 (2H, brs), 1.08 (9H, s).

B. 2-tert-Butyl 1,3,4-oxadiazole t-tert-Butyl 1,3,4-oxadizole was prepared as described above.

C. 1-[2-(5-tert-Butyl)-1,3,4-oxadiazolyl]-2-(S)-(tert-butoxycarbonylamino)-3-methylbutan-1-ol To a solution of 2-tert-Butyl-1,3,4-oxadiazole (62.1 g) in tetrahydrofuran (1650 ml) was added n-butyllithium in hexane (1.6 M, 307.8 ml) dropwise at −78° C. under an atmosphere of argon. The mixture was stirred for 40 min at −78° C., magnesium bromide diethyl etherate (127.2 g) was added, and the resulting mixture was allowed to warm to −45° C. After 1.5 hours, a solution of 2-(S)-[N-(tert-butoxycarbonyl)amino]-3-methylbutanal (90 g) in tetrahydrofuran (60 ml) was added dropwise at −45° C. and allowed to warm to −15° C. The reaction mixture was quenched by addition of a saturated aqueous solution of ammonium chloride, and extracted with ethyl acetate. The extract was washed with water (x3) and a saturated aqueous solution of sodium chloride, dried over anhydrous sodium sulfate and concentrated. The residue was purified by column chromatography on silica gel (Merck 7734) (ethyl acetate:hexane= 1:20→1:1) to give 1-[2-(5-tert-butyl)-1,3,4-oxadiazolyl]-2-(S)-(tert-butoxycarbonylamino)-3-methylbutan-1-ol (78.6 g) having the following physical data.

TLC: $R_f$=0.42, hexane:ethyl acetate (1:1).

$^1$H NMR (CDCl$_3$): δ 5.16–4.90 (2H, m), 4.67 (1H, m), 4.23 (1H, m), 3.90 (1H, m), 3.66 (1H, m), 1.98 (1H, m), 1.42, 1.41 and 1.36 (total 18H, each s), 1.13–0.90 (6H, m).

D. 1-[2-(5-tert-Butyl)-1,3,4-oxadiazolyl]-2-(S)-amino-3-methylbutan-1-ol Hydrochloride To a solution of 1-[2-(5-tert-butyl)-1,3,4-oxadiazolyl]-2-(S)-(tert-butoxycarbonylamino)-3-methylbutan 1-ol (76.3 g) in dioxane (200 ml) was added 4N hydrochloric acid in dioxane solution (1000 ml) at 0° C. The reaction mixture was concentrated under reduced pressure. The residue was solidified with diethyl ether. The solid was azeotroped with benzene several times to give 1-[2-(5-tert-butyl)-1,3,4-oxadiazolyl]-2-(S)-ainino-3-methylbutan-1-ol hydrochloride (66.1 g) having the following physical data.

TLC: $R_f$=0.30, chloroform:methanol (10:1);

$^1$H NMR (CDCl$_3$): δ 8.50–8.10 (2H, br), 7.10–6.80 (1H, br), 5.55–5.35 (1H, m), 3.95–3.60 (2H, m), 2.10 (1H, m), 1.41 (9H, s), 1.20–1.00 (6H, m).

E. 2-[6-Oxo-2-(4-fluorophenyl)-1,6-dihydro-1-pyrimidinyl]-N-[1-(2-[5-tert-butyl-1,3,4-oxadiazol] hydroxymethyl-)2-(S)-methylpropyl]acetamide.

To a solution of 1-[2-(5-tert-butyl)-1,3,4-oxadiazolyl]-2-(S)-amino-3-methylbutan-1-ol hydrochloride (10.76 g), [6-oxo-2-(4flurophenyl)-1,6-dihydro-1-pyrimidinyl]acetic acid (8.63 g) and 1-hydroxybenzotriazole (5.85 g) in dimethylformamide (100 ml) was added 1-ethyl-3-[3-dimethylamino)propyl]carbodiimide (7.33 g) at 0° C. To the resulting mixture was added 4-methylmorpholine (4.21 ml) at the same temperature. The reaction mixture was stirred for 17 hours at room temperature. The reaction was quenched by addition of water, extracted with ethyl acetate (x3). The extract was washed with aqueous 10% citric acid solution, a saturated aqueous solution of sodium hydrogencarbonate, water and a saturated aqueous solution of sodium chloride. The organic phase was dried over anhydrous sodium sulfate and concentrated under reduced pressure to 2-[6-oxo-2-(4-fluorophenyl)-1,6-dihydro-1-pyrimidinyl]-N-[1-(2-[5-tertbutyl1,3,4-oxadiazolyl]hydroxymethyl)-2-(S)-methylpropyl]acetamide (14.6 g) having the following physical data.

TLC: $R_f$=0.40, chloroform:methanol (10:1);

$^1$H NMR (DMSO-d$_6$): δ 8.00 and 7.94 (each 1H, each d, J=6.6 Hz), 7.71 and 7.55 (each 2H, each m), 7.19 and 7.18 (each 2H, each J=6.6 Hz), 6.43 and 6.38 (each 1H, each d, J=6.6 Hz), 5.13 (1H, d, J=2.2 Hz), 5.05 (1H, d, J=4.4 Hz), 4.54 (2H, s), 4.43 (2H, m), 4.31 (1H, m), 4.04 (1H, m), 2.20–1.52 (1H, m), 1.41 and 1.37 (each 9H, each s), 1.08, 1.00, 0.94 and 0.92 (each 3H, each d, J=6.6 Hz).

Example 5

2-[5-Benzyloxycarbonylamino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide The compound was prepared using a similar oxidative procedure as described in Example 1 utilizing 2-[5-benzyloxycarbonylamino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]hydroxymethyl)-2-(S)-methylpropyl]acetamide for the 2° alcohol. The title compound, 2-[5-benzyloxycarbonylamino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide, gave the following physical data.

TLC: $R_f$=0.66, chloroform:methanol (10:1);

$^1$H NMR (CDCl$_3$): δ 8.76 (1H, brs), 7.63–7.52 (2H, m), 7.49 (1H, brs), 7.38 (5H, brs), 7.13 (2H, t, J=8.6 Hz), 6.82–6.74 (3H, m), 6.71 (1H, brd, J=8.6 Hz), 5.94 (2H, s), 5.42 (1H, dd, J=8.6, 5.0 Hz), 5.22 (2H, s), 4.58 (2H, brs), 2.50 (1H, m), 1.83 (6H, s), 1.05 and 0.86 (each 3H, each d, J=7.0 Hz).

The intermediate 2-[5-benzyloxycarbonylamino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]hydroxymethyl)-2-(S)-methylpropyl]acetamide was prepared in an analoguous manner as described in Example 1 E using [5-benzyloxycarbonylamino-6-oxo-2-(4-fluorophenyl)-1,6-dihydro-1-pyrimidinyl]acetic acid and 1-[2(α,α-dimethyl-3,4-methylenedioxybenzyl)-1,3,4-oxadiazolyl]-2-(S)-amino-3-methylbutan-1-ol hydrochloride. The intermediate 1-[2-(α,α-dimethyl-3,4-methylenedioxybenzyl)-1,3,4-oxadiazolyl]-2-(S)-amino-3-methylbutan-1-ol hydrochloride was prepared using a similar procedure as described in Example 1 D. The heterocyclic intermediate 2-(α,α-dimethyl-3,4-methylenedioxybenzyl)-1,3,4-oxadiazole gave the following physical data.

TLC: $R_f$=0.69, chloroform:methanol (10:1).

$^1$H NMR (CDCl$_3$): δ 8.30 (1H, s), 6.78 (1H, brs), 6.74(2H, brs), 5.94 (2H, s), 1.81 (6H, s).

Example 6

2-[5Amino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(R,S)-methylpropyl]acetamide To 2-[5-(benzyloxycarbonylamino)-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide (1.42 g) was added 30% hydrobromic acid in acetic acid solution (50 ml). The reaction mixture was stirred for 1 hour at room temperature. The reaction mixture was quenched by addition of ice water, extracted with ethyl acetate (x2). The combined extracts were washed with water (x2) and a saturated aqueous solution of sodium chloride. The organic phase was dried over anhydrous sodium sulfate, filtered and concentrated under reduced pressure. The residue was purified by column chromatography on silica gel using a gradient elution of 50 to 100% ethyl acetate/hexane to give 2-[5-amino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(R,S)-methylpropyl]acetamide (457 mg) having the following physical data.

TLC: $R_f$=0.39, ethyl acetate.

$^1$H NMR (CDCl$_3$): δ 7.53 (2H, dd, J=8.8, 5.3 Hz), 7.48 (1H, s), 7.06 (2H, t, J=8.8 Hz), 6.90 (1H, brd, J=8.4 Hz), 6.84–6.70 (3H, m), 5.95 (2H, s), 5.43 (1H, dd, J=8.4, 4.8 Hz), 4.63 and 4.54 (each 1H Abq, J=15.0 Hz), 4.05 ((2H, brs), 2.51 (1H, m), 1.84 (6H, s), 1.06 and 0.87 (each 3H, each d, J=7.0 Hz).

Example 7

2-[5-Benzyloxycarbonylamino-6-oxo-2-phenyl-1-1,6-dihydro-1-pyrimidinyl]-N-[1-(2-[5-(α,α-dimethyl-3,4-methylenedioxybenzyl)-1,3,4-oxadiazolyl]carbonyl)-2-(R,S)-methylpropyl]acetamide The compound was prepared using a similar oxidative procedure as described in Example 1 utilizing 2-[5-benzyloxycarbonylamino-6-oxo-2-phenyl-1,6-dihydro-1-pyrimidinyl]-N-[1-(2-[5(α,α-dimethyl-3,4-methylenedioxybenzyl)-1,3,4-oxadiazolyl]hydroxymethyl)-2-(S)-methylpropyl]acetamide for the 2° alcohol. The title compound, 2-[5-benzyloxycarbonylamino-6-oxo-2-phenyl-1,6-dihydro-1-pyrimidinyl]-N-[1-(2-[5-(α,α-dimethyl-3,4-methylenedioxybenzyl)-1,3,4-oxadiazolyl]carbonyl)-2-(R,S)-methylpropyl]acetamide gave the following physical data.

TLC: $R_f$=0.34, hexane:ethyl acetate (1:1).

$^1$H NMR (CDCl$_3$): δ 8.78 1H, brs), 7.60–7.30 (1H, m), 6.78 (3H, m), 6.68 (1H, d, J=8.8 Hz), 5.94 (2H, s), 5.42 (1H, dd, J=8.8, 4.8 Hz), 5.23 (2H, s), 4.65 and 4.57 (2H, Abq, J=15.0 Hz), 2.49 (IH, m), 1.83 (6H, s), 1.04 (3H, d, J=6 Hz), 0.84 (3H, d, J=5.8 Hz).

The intermediate 2-[5-benzyloxycarbonylamino-6-oxo-2phenyl-1,6-dihydro-1-pyrimidinyl]-N-[1-(2-[5-(α,α-dimethyl-3,4-methylenedioxybenzyl)-1,3,4-oxadiazolyl]hydroxymethyl)-2-(S)-methylpropyl]acetamide was prepared in an analogous manner as described in Example 1 E using 5-benzyloxycarbonylamino-6-oxo-2-phenyl-1,6-dihydro-1-pyrimidinyl]acetic acid and 1-[2-(α,α-dimethyl-3,4-methylenedioxybenzyl)-1,3,4-oxadiazolyl]-2-(S)-amino-3-methylbutan-1-ol hydrochloride. The intermediate 1-[2-(α,α-dimethyl-3,4-methylenedioxybenzyl)-1,3,4-oxadiazolyl]-2-(S)-amino-3-methylbutan-1-ol hydrochloride was prepared using a similar procedure as described in Example 1 D. The heterocyclic intermediate 2-(α,α-dimethyl-3,4-methylenedioxybenzyl)-1,3,4-oxadiazole gave the following physical data.

TLC: $R_f$=0.69, chloroform:methanol (10:1).

$^1$H NMR (CDCl$_3$): δ 8.30 (1H, s), 6.78 (1H, brs), 6.74(2H, brs), 5.94 (2H, s), 1.81 (6H, s).

Example 8

2-[5-Amino-6-oxo-2-phenyl-1,6-dihydro-1-pyrimidinyl]-N-[1-(2-[5-(α,α-dimethyl-3,4-methylenedioxybenzyl)-1,3,4-oxadiazolyl]carbonyl)-2-(R,S)-methylpropyl]acetamide The compound was prepared using a similar procedure as described in Example 3 utilizing 2-[5-benzyloxycarbonylamino-6-oxo-2-phenyl-1,6-dihydro-1-pyrimidinyl]-N-[1-(2-[5(-α, α-dimethyl-3,4-methylenedioxybenzyl)-1,3,4-oxadiazolyl]carbonyl)-2-(S)-methylpropyl]acetamide. The title compound 2-[5-Amino-6-oxo-2-phenyl-1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide gave the following physical data.

TLC: $R_f$=0.40, ethyl acetate.

¹H NMR (CDCl₃): δ 7.59–7.34 (5H, m), 7.50 (1H, s), 6.86 (1H, d, J=8.2 Hz), 6.86–6.72 (3H, m), 5.95 (2H, s), 5.43 (1H, dd, J=8.2 and 4.8 Hz), 4.66 1H, d, J=15.4 Hz), 4.56 (2H, f, J=15.4 hz), 4.05 (2h, brs), 2.62–2.36 (1H, m), 1.84 (6H, s), 1.05(3H, d, J=7.0 Hz), 0.85 (3H, d, J=7.0 Hz).

Example 9

2-[6-oxo-2-phenyl-1,6-dihydro-1-pyrimidinyl]-N-[1-(2-[5-(α,α-dimethyl-3,4-methylenedioxybenzyl)-1,3,4-oxadiazolyl|carbonyl)-2-(R,S)-methylpropyl] acetamide TLC: R$_f$=0.46, ethyl acetate.
¹H NMR (CDCl₃): δ 8.01 (1H, d, J=6.6 Hz), 7.65–7.35 (5H, m), 6.87 (1H, d, J=8.6 ,Hz), 6.85–6.70 (3H, m), 6.49 (1H, d, J=6.6 Hz), 5.95 (2H, s), 5.42 (1H, dd, J=8.6 and 5.0 Hz), 4.67 (1H, d, J=15.2 Hz), 4.54 (1H, d, J=15.2 Hz), 2.63–2.37 (1H, m), 1.84 (6H, s), 1.05 (3H, d, J=6.8 Hz), 0.85 (3H, d, J=6.8 Hz)

Example 10

2-[6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(R,S)-methylpropyl]acetamide TLC: R$_f$=0.43, ethyl acetate.
¹H NMR (CDCl₃): δ 7.99 (1H, d, J=6.6 Hz), 7.63 (2h, dd, J=8.6, 5.2 Hz), 7.14 (2H, t, J=8.6 Hz), 6.93 (1H, brd, J=8.6 Hz), 6.84–6.70 (3H, m), 6.49 (1H, d, J=6.6 Hz), 5.95 (2H, s), 5.41 (1H, dd, J=8.6, 5.0 Hz), 4.64 and 4.53 (each 1H, Abq, J=15.0 Hz), 2.50 (1H, m), 1.84 (6H, s), 1.06 and 0.87 (each 3H, each d, J=7.0 Hz).

Example 11

2-[6-oxo-2-(4-fluorophenyl)1,6-dihydro-1-pyrimidinyl]-N-[1-(2-[5-(α,α-dimethylbenzyl)-1,3,4-oxadiazolyl]carbonyl)-2-(R,S)-methylpropyl] acetamide The compound was prepared using a similar oxidative procedure as described in Example 1 utilizing 2-[6-oxo-2-(4-fluorophenyl)-1,6-dihydro-1-pyrimidinyl]-N-[1-(2-[5-(α,α-dimethylbenzyl)-1,3,4-oxadiazolyl]hydroxymethyl)-2-(S)-methylpropyl]acetamide for the 2° alcohol. The title compound, 2-[6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide, gave the following physical data.

TLC: R$_f$=0.42, ethyl acetate.
¹H NMR (CDCl₃): δ 7.99 (1H, d, J=6.5 Hz), 7.62 (2H, m), 7.40–7.20 (5H, m), 7.14 (2H, t, J=8.8 Hz), 6.89 (1H, brd, J=8.6 Hz), 6.49 (1H, d, J=6.5 Hz), 5.42 (1H, dd, J=8.6, 5.0 Hz), 4.61 and 4.54 (each 1H, each d, J=15.0 Hz), 2.50 (1H, m), 1.88 (6H, s), 1.06 and 0.86 (each 3H, each d, J=6.7 Hz).

The intermediate 2-[6-oxo-2-(4-fluorophenyl)-1,6-dihydro-1-pyrimidinyl]-N-[1-(2-[5-(α, α-dimethylbenzyl)-1,3,4-oxadiazolyl]hydroxymethyl)-2-(S)-methylpropyl] acetamide was prepared in an analoguous manner as described in Example 1 E using [6-oxo-2-(4-fluorophenyl) 1,6-dihydro-1-pyrimidinyl]acetic acid and 1-[2-(α,α-dimethylbenzyl)-1,3,4-oxadiazolyl]-2-(S)-amino-3-methylbutan-1-ol hydrochloride. The intermediate 1-[2-(α, α-dimethyl-3,4-methylenedioxybenzyl)-1,3,4-oxadiazolyl]-2-(S)-amino-3-methylbutan-1-ol hydrocloride was prepared using a similar procedure as described in Example 1 D. The heterocyclic intermediate 2-(α,α-dimethylbenzyl)-1,3,4-oxadiazole gave the following physical data.

TLC: R$_f$=0.43, ethyl acetate:hexane (1:2).
¹H NMR (CDCl₃): δ 8.31 (1H, s), 7.40–7.14 (5H, m), 1.86 (6H, s).

Example 12

2-[6-oxo-2-phenyl-1,6-dihydro-1-pyrimidinyl]-N-[1-(2-[5-(α,α-dimethylbenzyl)-1,3,4-oxadiazolyl] carbonyl)-2-(R,S)-methylpropyl]acetamide The compound was prepared using a similar oxidative procedure as described in Example 4 utilizing 2-[6-oxo-2-phenyl-1,6-dihydro-1-pyrimidinyl]-N-[1-(2-[5-(α,α-dimethylbenzyl)-1,3,4-oxadiazolyl]hydroxymethyl)-2-(S)-methylpropyl]acetamide for the 2° alcohol. The title compound, 2-[6-oxo-2-phenyl-1,6-dihydro-1-pyrimidinyl]-N-[1-(2-[5-(α,α-dimethylbenzyl)-1,3,4-oxadiazolyl] carbonyl)-2-(S)-methylpropyl]atetamide, gave the following physical data.

TLC: R$_f$=0.44, ethyl acetate.
¹H NMR (CDCl₃): δ 8.02 (1H, d, J=6.5 Hz), 7.64–7.24 (10H, m), 6.82 (1H, brd, J=8.4 Hz), 6.50 (1H, d, J=6.5 Hz), 5.44 (1H, dd, J=8.4, 4.8 Hz), 4.63 and 4.56 (each 1H, each d, J=15.4 Hz), 2.50 (1H, m), 1.89 (6H, s), 1.06 and 0.86 (each 3H, each d, J=6.8 Hz).

The intermediate 2-[6-oxo-2-phenyl-1,6-dihydro-1-pyrimidinyl]-N-[1-(2-[5-(α, α-dimethylbenzyl)-1,3,4-oxadiazolyl]hydroxymethyl)-2-(S)-methylpropyl]acetamide was prepared in an analoguous manner as described in Example 1 E using [6-oxo-2-phenyl-1,6-dihydro-1-pyrimidinyl]acetic acid and 1-[2-(α,α-dimethylbenzyl)-1,3,4-oxadiazolyl]-2-(S)-amino-3-methylbutan-1-ol hydrochloride.

Example 13

2-[5-Methyloxycarbonylamino-6-oxo-2-phenyl-1,6-dihydro-1-pyrimidinyl]-N-[1-(2-[5-(tert-butyl)-1,3,4-oxadiazolyl]carbonyl)-2-(R,S)methylpropyl] acetamide.

Prepared by a procedure analogous to that of Example 7. The product had the following physical data.

TLC: Rf=0.57 methanol:chloroform, 1:10.
¹H NMR (200 MHz, CDCl₃): 8.78 (brs, 1H, H of pyrimidinone), 7.62–7.40 (m, 6H, NH and aromatic Hs), 6.73 (brd, J=8.4 Hz, 1H, CONH), 5.45 (dd, J=8.4, 5.0 Hz, 1H, α CH of Val), 4.67 and 4.61 (each d, J=15.0 Hz, each 1H, CH₂ of Gly), 3.81 (s, 3H, CH₃O), 2.51 (m, 1H, CH of iso-Pr), 1.48 (s, 9H, CH₃s of t-Bu), 1.07 and 0.88 (each d, J=6.8 Hz, each 3H, CH3s of iso-Pr).

Example 14

In Vitro Inhibition of Elastase

The following protocol was used to determine inhibitory activity of compounds described herein. The elastase used in the protocol was derived from human sputum (HSE). A mother solution of the HSE enzyme was prepared from commercially available HSE (875 U/mg protein, SE-563, Elastin Product Co., Inc, Missouri, USA) by diluting with saline to 1,000 U/ml, which was further diluted to 2 U/ml at 0° C. prior to use.

A solution was prepared by mixing 100 μl 0.2 M HEPES-NaOH buffer (pH 8.0), 40 μl 2.5 M NaCl, 20 μl 1% polyethyleneglycol 6000, 8 μl distilled water, 10 μl of a DMSO solution of inhibitor and 2 μl solution of N-methoxysuccinyl-Ala-Ala-Pro-Val-p-nitroaniline (at concentrations of 100, 200 and 400 μM). The solution was incubated for 10 minutes at 37° C. To this was added an enzyme solution of HSE (elastase derived from human sputum). The resulting mixture was subjected to the following rate assay.

Optical density (SPECTRA MAX 250, Molecular Devices) at 405 nm due to p-nitroaniline generated by the enzyme reaction was measured at 37° C. in order to measure the reaction rate during the period that the production rate of p-nitroaniline remains linear. The rate, mO.D./min., was measured for 10 minutes at 30 second intervals immediately after the addition of the enzyme solution. $IC_{50}$ values were determined by log-logit method and converted to $K_1$ values by Dixson plot method. The compounds are presented in Table 2 showing the inhibition activity ($K_1$ values, nM) against HNE.

| 0.2M tris-HCl buffer (pH 8.0) | 100 μl |
| 2.5M NaCl | 40 μl |
| Distilled water | 36 μl |
| 50 mM solution of a substrate (*) | 4 μl |
| The Sample | 20 μl |

*N-Methylsuccinyl-Ala-Ala-Pro-Va-lp-nitroaniline

A test sample mixed with 1-methyl-2-pyrrolidone instead of the substrate is regarded as Substrate (−). A test sample mixed with saline instead of the Sample is regarded as Blank. The remaining elastase activity in the Sample is calculated according to the following:

TABLE 2

Biological Activity

| Example | Name | $K_1$ (nM) |
|---|---|---|
| 1 | Methyloxycarbonyl-L-valyl-N-[1-(2-[5-(tert-butyl)-1,3,4-oxadiazolyl]carbonyl)-2-(S)-methylpropyl]-L-prolinamide | 3.0 |
| 2 | Methyloxycarbonyl-L-valyl-N-[1-(2-[5-(α,αdimethylbenzyl)oxadiazolyl]carbonyl)-2-(S)-methylpropyl]-L-prolinamide. | 1.32 |
| 3 | Methyloxycarbonyl-L-valyl-N-[1-(2-[5-(α,αdimethyl-3,4-methylenedioxybenzyl)-1,3,4-oxadiazolyl]carbonyl)-2-(S)-methylpropyl]-L-prolinamide. | 0.24 |
| 4 | 2-[6-Oxo-2-(4-fluorophenyl)-1,6-dihydro-1-pyrimidinyl]-N-[1-(2-[5-tert-butyl-1,3,4-oxadiazolyl]carbonyl-2-(R,S)-methylpropyl]acetamide | 44.4 |
| 6 | 2-[5-Amino-6-Oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl-2-(R,S)-methylpropyl]acetamide | 0.51 |
| 8 | 2-[5-Amino-6-Oxo-2-phenyl-1,6-dihydro-1-pyrimidinyl]-N-[1-(2-[5-α,α-dimethyl-3,4-methylenedioxybenzyl)-1,3,4-oxadiazolyl]carbonyl-2-(R,S)-methylpropyl]acetamide | 1.06 |
| 9 | 2-[6-Oxo-2-phenyl-1,6-dihydro-1-pyrimidinyl]-N-[1-(2-[5(α,α-dimethyl-3,4-methylenedioxybenzyl)-1,3,4-oxadiazolyl]carbonyl-2-(R,S)-methylpropyl]acetamide | 0.34 |
| 10 | 2-[6-Oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl-2-(R,S)-methylpropyl]acetamide | 1.53 |
| 11 | 2-[6-Oxo-2-(4-fluorophenyl)-1,6-dihydro-1-pyriidinyl]-N-[1-(2-[5-(α,α-dimethylbenzyl)-1,3,4-oxadiazolyl]carbonyl)-2-(R,S)-methylpropyflacetamide | 5.34 |
| 12 | 2-[6-Oxo-2-phenyl-1,6-dihydro-1-pyrimidinyl]-N-[1-(2-[5-(α,α-dimethylbenzyl)-1,3,4-oxadiazolyl]carbonyl)-2-(R,S)-methylpropyl]acetamide | 1.83 |

Example 15

Ex Vivo Inhibition of Elastase

Sixty (60) minutes after the oral administration of an inhibitor with an appropriate vehicle, a blood sample (0.9 ml) is collected through the abdominal aorta by a syringe containing 0.1 ml of a 3.8% sodium citrate solution.

The blood sample is processed as follows: 60 μl of (final 0.1–1 mg/ml) a suspended solution of opsonized zymosan in Hank's buffer is added to the preincubated whole blood (540 μl) for 5 minutes at 37° C., and the resulting mixture is incubated for 30 minutes at the same temperature. The reaction is terminated by immersing the test tube into ice water. The reaction mixture is then centrifuged at 3,000 rpm for 10 minutes at 4° C. Twenty (20) μl of each of the resulting supernatant (the Sample) is measured for elastase activity.

The mixture consisting of the following components is incubated for 24 hours at 37° C., and then optical density is measured at 405 nm:

optical density of Substrate (+)−(optical density of Substrate (−)+ optical density of Blank)

as a total production of p-nitroaniline over 24 hours based on a standard curve for the amount of p-nitroaniline.

An average activity is calculated based on the test sample of 5–6 animals. An agent at 3, 10 or 30 mg/kg is orally given by a forced administration to a 24 hour fasted animal at 60 minutes before the blood sampling. Optical density is measured by SPECTRA MAX 250 (Molecular Devices).

Some representative results are given in Table 3.

TABLE 3

Representative Results of Ex-Vivo Studies

| | Percent Inhibition at Indicated Dosage | | |
|---|---|---|---|
| Example | 3 mg/kg | 10 mg/kg | 30 mg/kg |
| 2 | 7% | 9% | 62% |
| 3 | 44% | 69% | 99% |

What is claimed is:

1. The compound, 2-[5-methyloxycarbonylamino-6-oxo-2-phenyl-1,6-dihydro-1-pyrimidinyl]-N-[1-(2-[5-tert-butyl]-1,3,4-oxadiazolyl)carbonyl-2-(R,S)-methylpropyl]acetamide.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Sequence is a known commercially available substrate for elastases.
<221> NAME/KEY: BLOCKED
<222> LOCATION: (1)...(1)
<223> OTHER INFORMATION: N-terminal Methoxysuccinyl group.
<221> NAME/KEY: BLOCKED
<222> LOCATION: (4)...(4)
<223> OTHER INFORMATION: C-terminal p-nitroaniline

<400> SEQUENCE: 1

Ala Ala Pro Val
 1